US010856917B2

(12) United States Patent
Wingenfeld et al.

(10) Patent No.: US 10,856,917 B2
(45) Date of Patent: Dec. 8, 2020

(54) ARTHRODESIS IMPLANT

(71) Applicant: Syntellix AG, Hannover (DE)

(72) Inventors: Carsten Wingenfeld, Alfter (DE); Robert Schavan, Hannover (DE); Jan-Marten Seitz, Hannover (DE); Arne Lucas, Hannover (DE)

(73) Assignee: SYNTELLIX AG, Hannover (DE)

( * ) Notice: Subject to any disclaimer, the term of this patent is extended or adjusted under 35 U.S.C. 154(b) by 57 days.

(21) Appl. No.: 15/571,612

(22) PCT Filed: May 4, 2016

(86) PCT No.: PCT/EP2016/060017
§ 371 (c)(1),
(2) Date: Nov. 3, 2017

(87) PCT Pub. No.: WO2016/177790
PCT Pub. Date: Nov. 10, 2016

(65) Prior Publication Data
US 2018/0140338 A1 May 24, 2018

(30) Foreign Application Priority Data
May 6, 2015 (DE) .................. 10 2015 107 056

(51) Int. Cl.
A61B 17/72 (2006.01)
A61F 2/42 (2006.01)

(52) U.S. Cl.
CPC ...... A61B 17/7258 (2013.01); A61B 17/7291 (2013.01); A61F 2/4241 (2013.01); A61F 2002/4243 (2013.01)

(58) Field of Classification Search
CPC ............ A61F 2/4241; A61F 2002/4243; A61F 2002/4246; A61F 2002/4248; A61B 17/7291
See application file for complete search history.

(56) References Cited

U.S. PATENT DOCUMENTS 5,725,581 A * 3/1998 Brånemark ......... A61F 2/30721
606/304
7,041,106 B1 * 5/2006 Carver ............... A61B 17/7291
606/309

(Continued)

FOREIGN PATENT DOCUMENTS

DE  10 2008 045 291 A1  3/2010
DE  20 2008 018 002 U1  4/2011

(Continued)

OTHER PUBLICATIONS

International Search Report issued in connection with PCT Application No. PCT/EP2016/060017, dated Aug. 8, 2016.

(Continued)

Primary Examiner — David H Willse
Assistant Examiner — Javier G Blanco
(74) Attorney, Agent, or Firm — Steven M. Shape; Dennemeyer & Associates, LLC

(57) ABSTRACT

A resorbable implant for osteosynthesis for stiffening in a central joint (e.g., the proximal interphalangeal joint referred to as PIP) during arthrodesis or for stiffening in an end joint (e.g., the distal interphalangeal joint referred to as DIP) during arthrodesis and for osteosynthesis and stabilization of fractures of small bones of the human skeleton includes two shafts placed against each other. At least one fixing aid is located between the shafts. The fixing aid protrudes beyond a diameter of the shafts. Each shaft may have longitudinal grooves and transverse grooves. The implant is a magnesium-based material which can be resorbed by the human body. The disclosed implant has a relatively high tensile strength, excellent stability, optimal healing properties, and an optimally adapted resorption speed.

16 Claims, 3 Drawing Sheets

(56) References Cited

U.S. PATENT DOCUMENTS

| | | | |
|---|---|---|---|
| 8,454,706 B2* | 6/2013 | de Beaubien | A61F 2/36 623/23.39 |
| 9,326,804 B2* | 5/2016 | Biedermann | A61B 17/68 |
| 2009/0081313 A1* | 3/2009 | Aghion | A61L 27/047 424/641 |
| 2010/0198332 A1* | 8/2010 | Gerold | A61L 31/022 623/1.15 |
| 2011/0301653 A1 | 12/2011 | Reed | |
| 2012/0089197 A1* | 4/2012 | Anderson | A61B 17/7233 606/310 |
| 2013/0131822 A1 | 5/2013 | Lewis | |
| 2014/0236155 A1* | 8/2014 | Neubert | A61L 31/022 606/77 |
| 2014/0309747 A1* | 10/2014 | Taylor | A61F 2/42 623/21.11 |
| 2014/0343616 A1 | 11/2014 | Sellers | |
| 2015/0374503 A1* | 12/2015 | Lovick | A61B 17/7291 623/23.5 |

FOREIGN PATENT DOCUMENTS

| | | |
|---|---|---|
| DE | 101 28 100 A1 | 12/2012 |
| DE | 10 2011 082 210 A1 | 3/2013 |
| EP | 0 966 979 B1 | 12/1999 |
| WO | 01/17445 A1 | 3/2001 |
| WO | 2010/017959 A2 | 2/2010 |
| WO | WO-2013034466 A1 * | 3/2013 ........... A61L 31/022 |
| WO | 2013/177252 A1 | 11/2013 |

OTHER PUBLICATIONS

International Preliminary Report on Patentability issued in connection with PCT Application No. PCT/Ep2016/060017, dated Nov. 16, 2017.

"Prospektive Untersuchung interner Osteosynthesen mit resorbierbaren Implantaten in der Vorfußchirurgie" von Panagiotis Bouliopoulos, Medizinische Fakultät der Ludwig-Maximilians—Universität, München (2005).

Richard A. Lindtner, et al. "Comparative biomechanical and radiological characterization of osseointegration of abiodegradable magnesium alloy pin and acopolymeric control for osteosynthesis," Journal of the Mechanical Behavior of Biomedical Materials 28 (2013) 232-243, published Aug. 20, 2013.

Zeeshan Sheikh, et al. "Biodegradable materials for bone repair and tissue engineering applications," Open Access Materials ISSN 1996-1944, published Aug. 31, 2015.

* cited by examiner

ARTHRODESIS IMPLANT

CROSS-REFERENCE TO RELATED APPLICATIONS

This is a 35 U.S.C. 371 National Stage Patent Application of International Application No. PCT/EP2016/060017, filed May 4, 2016, which claims priority to German application 10 2015 107 056.1, filed May 6, 2015, each of which is hereby incorporated by reference in its entirety.

The invention relates to an implant for the osteosynthesis of the PIP arthrodesis or the DIP arthrodesis of small joints and for the osteosynthesis and stabilisation of fractures of small bones of the human skeleton, said implant being resorbable by the human body. The implant consists of two shafts placed against each other. At least one fixing aid is located between the shafts, said fixing aid protruding beyond the diameter of the shaft. Each shaft can optionally have longitudinal grooves and transverse grooves. The implant consists of a magnesium-based material which can be resorbed by the human body. The invention provides an implant which has an extremely high tensile strength, excellent stability, optimal healing properties, and an optimally adapted resorption speed.

Malpositions of toe or finger joints are prevalent disorders of the human skeleton. They are partly hereditary, partly acquired through unfavourable living conditions, perhaps by wearing inadequate footwear, one-sided constant loading of individual joints such as standing for long periods on hard ground and the suchlike. Common appearances are the clinical picture of the hallux valgus and the so-called hammertoe associated with this. As a result of osseous deformities and malpositions, severe pain of the joints occurs with limitations to mobility, accompanied by swelling and inflammatory symptoms. Those affected consequently avoid sports activities, then running, walking or gripping and finally often all types of movement, sparking a vicious circle as a disastrous result because the problems develop and intensify further when there is insufficient movement.

A possibility of treatment consists in correcting the painful toe joint through surgical intervention in its position and orientation and then stiffening it. Stiffening in the central joint (proximal interphalangeal joint) is referred to as PIP arthrodesis, and stiffening in the end joint (distal interphalangeal joint) is referred to as DIP arthrodesis. The same applies to finger bones, wherein predominantly the central joint is stiffened there. Although the joint is fixed by stiffening, the pain is eliminated. As a result, the joint is no longer mobile, although the foot or the hand can on the whole be loaded again pain-free and moved, and thus the patient will return to improved mobility. For the foot both PIP and DIP arthrodeses are used, and predominantly a DIP arthrodesis is generally used for the hand.

For this in surgery of the hand and foot, the prior art knows wires and pins made from stainless steel or titanium—so-called Kirschner wires. These are placed temporarily and often percutaneously, and removed again in a second operation after a certain period of healing and adhesion of the joint. This treatment requires a second operation, which bears associated costs and physical and psychological stress for the patient.

In the course of progress of implant technology, pins, screws and plates have thus been developed which permanently fix the joint and are no longer removed. These implants which remain in the bone for life have diverse advantages. For the patient they provide relief since a second operation with the risks of anaesthesia and infection is not required. They also offer cost savings since no additional intervention and hospital stay is necessary. Primarily sterile nails, pins, screws, plates and shafts made from titanium, tantalum or stainless steel are used. The permanently placed implants, however, also have disadvantages in the fact that they can come loose. In the human body, most cells undergo constant depletion and rebuilding, the intensity and speed of which is linked to age. Even bone cells are regenerated. It is in particular with older people that problems of bone regeneration occur, commonly known by the term osteoporosis. Hormonal factors in combination with mineral deficiency can cause disorders in bone formation or bone regeneration. Then implants and prostheses which were initially firm can loosen and lead to various complaints, with the result that one day they will have to be operated on again. This precisely ought to have been prevented for long as possible. The disadvantage is that in the event of accidents to bones which are connected by means of such implants, very complicated comminuted fractures can occur.

An operational problem is that bone-connecting implants—are hard to fix particularly when a specific angle of curvature has to be maintained—during an operation, and they can move axially or rotate by small angles about the longitudinal axis. This poses considerable risk for surgical intervention because the operated joint is supposed to be fixed after the operation in that position which is physiologically appropriate. Fixing elements in the form of lugs, points, scores, grooves or rails offer a way out of this problem, which can be attached to the implant and assist the surgeon in positioning the implant precisely axially and in a rotationally fixed manner. However, such fixing elements cannot be attached to permanently implanted bone-connecting pins made of titanium, tantalum or stainless steel because in this case a spacer element permanently acts as a gap between the bones to be connected, which has a destabilising effect, prevents the healing process and prevents bone or joint fusion.

Permanently lying implants comprising high strength also have the further disadvantage that a stress shielding effect can arise. This is understood to mean the problem that firm bone implants introduce strong forces in the bone, as a result of which overloading occurs at certain points of the bone, while at the same time forces are kept away from the bone at other points, and the bone is thus relieved. However, bone requires constant and even stimulation with forces which is in the range of natural bone strength of 100 to 200 MPa in order to regenerate. If there is no stimulation, bone degradation and loosening occur over time. The stress shielding effect has far-reaching consequences. The healing process can slow down and the relieved bone can even recede. However, precisely this has to be avoided. The bone has to be built up, stabilised and healed.

To avoid these problems, so-called bioresorbable or biodegradable implants made of polyglycolides or polylactides are known from the prior art, which are gradually dissolved and degraded in the bone under the influence of tissue fluid and do not have to be surgically removed after healing. They are successively replaced by newly formed endogenous bone tissue. The treatment of toe joints by implants built from polylactides is described in the dissertation "Prospective Study of Internal Osteosyntheses With Resorbable Implants in Forefoot Surgery" by Panagiotis Bouliopoulos, medical faculty of the Ludwig Maximilian University, Munich (2005). It should be noted from the study that there are considerable advantages by replacing a permanently lying implant by means of a resorbable implant which gradually dissolves. In particular, the above-mentioned stress shielding effect is avoided, subjectively perceived foreign body feelings are reduced and any subsequent interventions due to fractures can easily be carried out.

However, polymeric substances also face disadvantages. A considerable disadvantage of implants based on polylactides is their low mechanical loading capacity. The tensile strength of lactide polymers is less 50 MPa. They also have low thermal stability. In the period of bone formation, for which approximately 12 weeks have to be estimated according to the patient's constitution, much depends on the mechanical loading capacity of the implant, which in the case of polymer implants has to be deemed insufficient. A further disadvantage is that an acidic environment is created around the implant during the hydrolytic degradation process of the polymers. This can act in a tissue-damaging manner and lead to the fact that the implant bed is not penetrated by bone. To some extent, holes remain in the bone over a longer period.

Instead of resorbable polymeric materials, magnesium alloys have already been used as resorbable metallic materials for some time in medical technology. Patent document EP 0 966 979 B1 describes the use of a magnesium alloy as a stent or wall support in blood vessels, without mentioning the composition of the alloy in more detail. Laid-open application DE 101 28 100 A1 describes various magnesium-based alloys as suitable for wires, pins, screws, plates, etc. in human and veterinary medicine. However, these alloys contain aluminum in proportions of up to 16 wt. %, and according to current understanding are not suitable as biodegradable implants due to the toxicity of aluminum (nerve damage, suspicion of triggering Alzheimer's disease). Utility model document DE 20 2008 018 U1 describes an implant based on a magnesium alloy containing yttrium, rare-earth elements and zirconium, although there are no indications as to how the implant must be designed to treat specific clinical pictures. However, only a simple screw shape is disclosed as an embodiment. Laid-open application DE 10 2011 082 210 A1 describes the production of biodegradable semi-finished products made from magnesium-based alloys in a complex, multi-stage powder-metallurgical process and mentions only the possibility of producing medical implants therefrom. However, there is no more detailed description of corresponding implants.

The aim of the present invention is, therefore, to avoid the described disadvantages of non-biodegradable implants and biodegradable implants based on lactide, wherein a biodegradable material based on a magnesium alloy is to be utilised as an implant for osteosynthesis of the PIP arthrodesis or of the DIP arthrodesis of small joints and for the osteosynthesis and stabilisation of fractures of small bones of the human skeleton. The object is achieved by an implant made of a metallic material based on magnesium, which is resorbable by the human body, the copper and aluminum content of which in each case is less than 0.20 wt. %, and wherein the implant consists of at least two shafts placed against each other which are connected to one another at an angle of 145 to 180 degrees, and wherein at least one fixing aid is provided between the shafts, which protrudes beyond the diameter of the shaft.

The invention thus relates to a resorbable metallic implant, especially for arthrodesis of small joints and bones or the osteosynthesis thereof on the basis of a magnesium material, which gradually dissolves in the body after fixing of the joint or of the bone and the fusion of the bones, is converted into organic substances and replaced by endogenous bone material. The magnesium ions formed during the degradation oxidise and are partially incorporated into the bone as oxides or hydroxides, are partially metabolised and are excreted via urine. The implant can be used on toe joints, toe and foot bones, on finger joints and in the case of fractures of the finger and foot bones. The two shafts of the implant are referred to as proximal and distal shaft, wherein the proximal shaft is that shaft which is directed towards the body centre, while the distal shaft is the shaft, which is directed away from the body centre.

The shafts of the implant are preferably conical. They can be equipped with stabilising means which are mounted in the longitudinal direction and can be formed, for example, by longitudinal grooves. These allow a narrow drilling channel adapted to the bone, as a result of which valuable bone substance is retained in particular and particularly in the case of small bones. The longitudinal grooves counteract a rotation, since they impress themselves into the intramedullary, somewhat softer tissue. The implant is thus extremely torsion-resistant. The milled-out portions increase the surface area, which is favourable for the initial adhesion or intermeshing of the implant with the bone tissue. The resorption rate can additionally be adapted by modifying the surface. It is particularly preferred if the number of longitudinal grooves is two to eight, preferably six. In an alternative embodiment, the stabilising means mounted in the longitudinal direction are designed as blades or wing-shaped elevations, which extend along the shafts.

Fixing aids are attached to the implant. These can have the shape of wing extensions. They serve as a stop during the insertion of the implant into the proximal bore and when the distal bone is applied to the implant. This allows the surgeon to optimally fix the implant during the operation, and also pre-drilling too deeply remains without restrictions for the optimum seat of the implant. A formation of gaps and thus the obstruction of fusion during the healing process does not have to be feared since the thin fixing aid rapidly dissolves. There are two to eight, but most preferably three, fixing aids. The fixing aids are preferably designed in the form of wing extensions. However, they can also have any other shape; thus, they can be formed, for example, as lugs, rails, scores or fixation points. The fixing aids are preferably arranged at equal distances around the shaft. Their thickness in the cross-section is 0.10 to 2.00 mm and they project radially beyond the shaft by 0.25 to 4.00 mm. It has been found to be advantageous if the thickness in the cross-section of the fixing aids is between 0.20 and 2.00 mm and the fixing aids protrude radially beyond the shaft by 0.50 to 4.00 mm. In addition, it has been found to be particularly advantageous if the thickness in the cross-section of the fixing aids is between 0.20 and 1.00 mm, and the fixing aids protrude radially beyond the shaft by 0.50 to 2.00 mm. In an extremely advantageous embodiment, the thickness in the cross section of the fixing aids is between 0.20 and 0.80 mm and the fixing aids project radially beyond the shaft by 0.50 to 1.00 mm. The fixing aids enable the operating surgeon to precisely position the implant and they dissolve in the course of the healing process and the resorption. The risk of gap formation between the interconnected bones, destabilisation of the operatively treated region and thus obstruction of the fusion are eliminated.

The implant consists of two shafts, a distal and a proximal shaft. These are connected to one another. They can, for example, be welded to one another or connected by a bioabsorbable adhesive. In one possible embodiment variant, the distal and proximal shaft are produced from one piece. In order to ensure optimum stability while considering the degradation and installation speed of the material, care must be taken to ensure that the length of the shafts in each case is 5.00 to 75.00 mm, the diameter of the shafts is 1.50 to 20.00 mm, the thickness of the fixing aids is 0.10 to 2.00 mm and the overhang of the fixing aids over the diameter of the shafts is 0.25 to 4.00 mm. It has been found that the length of the shafts is preferably in each case 5.00 to 15.00 mm, the diameter of the shafts is preferably 2.00 to 10.00 mm, the thickness of the fixing aids is preferably 0.20 to 1.00 mm and the overhang of the fixing aids over the diameter of the shafts is preferably 0.50 to 2.00 mm. A very particularly advantageous embodiment is characterised in that the length of the proximal shaft is 10.00 to 15.00 mm, the length of the distal shaft is 5.00 to 11.00 mm and the diameter of the two shafts is in each case 2.40 to 3.60 mm.

Angled implants are to be preferred for anatomical reasons, since they correspond to a physiological standard position of the bridged and thus deactivated joint. The angle spanned between the shafts is between 155 and 175 degrees, preferably between 160 and 175 degrees, and it is most preferably approximately 160 degrees. In another possible embodiment, the angle between the shafts is approximately 180 degrees.

Preferably, one of the shafts is additionally provided with transverse grooves. The transverse grooves serve in particular in intraoperative handling for axial stabilisation after the proximal portion of the implant has been introduced into the proximal bone. In the slightly flexible or intramedullary tissue, a positive fit is produced to some extent in the implant bed. After the implant has been introduced against the fixing aids, this form fit prevents the implant being unintentionally pulled out of the implant bed again. In this possible embodiment, no transverse grooves are to be introduced on the distal side of the implant. One advantage of this is the increase in safety in surgical technique. There are always reoccurring cases of implants being placed the wrong way round. The transverse grooves ensure that the administering physician can distinguish between the distal and the proximal shaft. In an alternative embodiment of the invention, both shafts are provided with transverse grooves so that a special hold is also created between the distal shaft and the bone.

The implant can be characterised in that a magnesium alloy from the alloy system MgYREZr is used as the resorbable material, i.e. the alloy comprises at least magnesium, zirconium, yttrium and other rare earth metals.

In one possible embodiment, the magnesium-based alloy contains 0.10 to 1.00 wt. % zirconium, 4.75 to 5.50 wt. % yttrium and 1.50 to 4.00 wt. % further rare earth metals. In a further possible embodiment, the magnesium alloy contains 0.10 to 1.00 wt. % zirconium, 3.70 to 4.30 wt. % yttrium and 2.40 to 4.40 wt. % further rare earth metals. Corresponding alloys have a tensile strength of 200 to 250 MPa. These alloys can be produced according to DIN EN 1753. It is very particularly advantageous if the alloys satisfy the parameters given for the materials EN-MC95310 or EN-MC95320 in DIN EN 1753.

In a particular embodiment, the magnesium alloy contains 0.10 to 2.50 wt. % zirconium, 0.01 to 0.80 wt. % zinc, 1.50 to 5.00 wt. % yttrium and 2.50 to 5.00 wt. % rare earth metals. As a result, an increased tensile strength of up to 300 MPa can be achieved.

The tensile strength of the listed magnesium alloys is thus significantly above the strength of the lactide polymers of max. 50 MPa. The tensile strength thereof is rather close to the tensile strengths and elasticity values which are measured on human bones. As a special feature of the present invention it should also be noted that all alloys have to be produced or purified such that the content of copper, aluminum, nickel and iron in each case is below 0.20 wt. % in the finished alloy so that toxic phenomena and an impairment of the corrosion properties can be reliably avoided. The content of copper, aluminum, nickel and iron is preferably less than 0.01 wt. %.

The compositions most preferably contain less than 0.01 wt. % aluminium, less than 0.20 wt. % zinc, less than 0.15 wt. % manganese, less than 0.20 wt. % lithium, less than 0.01 wt. % silicon, less than 0.01 wt. % iron, less than 0.03 wt. % copper and less than 0.005 wt. % nickel. In contrast to the toxic effect by impurities, the magnesium ions released during dissolution have different positive physiological effects in the body of the patient. Since the magnesium ions contribute to a stabilisation of the electrolyte balance during the phase of dissolution in the body, they have a positive effect on bone growth and release further various positive healing effects owing to influences on the nerve tissue in the operated region. The magnesium is excreted via the kidneys. Intoxication by an elevated magnesium level has never been reported.

In a departure from the preceding embodiments, the magnesium alloy in one possible embodiment for increasing the strength can be 0.50 to 5.00 wt. % lithium and/or 1.00 to 3.00 wt. % metallic zirconium.

The great advantage when using biodegradable magnesium implants according to the invention is that both a second operation for removing the implant and the need for a later second operation due to loosening of the implant are eliminated since it is completely degraded in the body. A further advantage is that magnesium-based bioresorbable implants have a considerably higher strength compared to polymeric lactide-based implants. In the healing phase lasting about twelve weeks after the operation, during which the implant still has to absorb most of the forces that occur, there is optimum stabilisation of the stiffened joint since the strength of the magnesium alloy is significantly above that of polymeric implant materials.

It is also advantageous that degradation of the magnesium implant proceeds so slowly that degradation of the implant proceeds at a rate which is matched to the build-up rate of the bone. The bone growth at the operating site and the degradation of the implant are in equilibrium. The newly formed bone tissue in this regard successively bears the forces that occur. Stress shielding effect is avoided. By means of the composition of the alloy it is also possible to influence the kinetics of the degradation and to adapt to the physiological conditions of certain indications or patient groups.

The invention is explained by the attached drawings.

Figure 1:
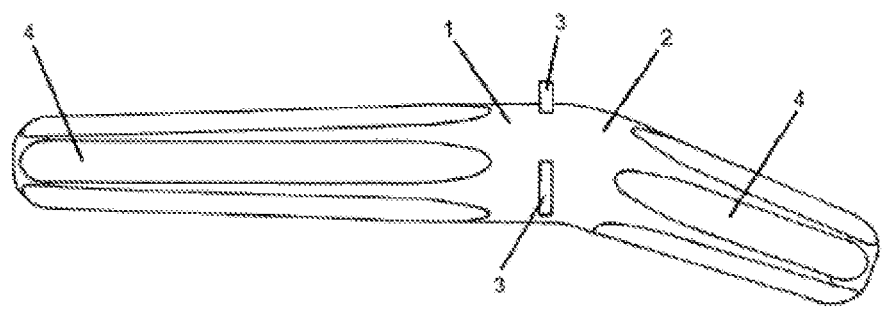
FIG. 1 shows a first embodiment of the invention in a side view.

FIG. 1 shows a first embodiment of the invention in a side view. The magnesium alloy used for production contains 0.10 to 2.50 wt. % zirconium, 0.01 to 0.80 wt. % zinc, 1.50 to 5.00 wt. % yttrium and 2.50 to 5 wt. % further rare earth metals. It consists of a proximal shaft (1) and a distal shaft (2). The length of the proximal shaft (1) is 12.40 millimetres and the length of the distal shaft (2) is 6.20 mm. The angle between the proximal shaft (1) and the distal shaft (2) is 160 degrees. Said angle is to be adapted to the physiological conditions of the patient and can, therefore, differ accordingly in other embodiments. Between the proximal shaft (1) and the distal shaft (2), three wing extensions are located as fixing aids (3). These have a thickness of 0.30 mm and a projection of 1.00 mm. The fixing aids (3) quickly dissolve after the operation so that a gap formation between the bones connected by the proximal shaft (1) and the distal shaft (2) is avoided. The shafts (1, 2) are each provided with six longitudinal grooves (4) which bring about an enlargement of the surface of the implant. This in turn influences the resorption rate of the implant. In addition, the longitudinal grooves (4) prevent the implant from rotating in the bone. The combination of the magnesium alloy according to the invention and the special structure results in an implant which has an extremely high tensile strength of up to 300 MPa, has excellent stability, best healing properties and an optimally adapted resorption rate.

Figure 2:
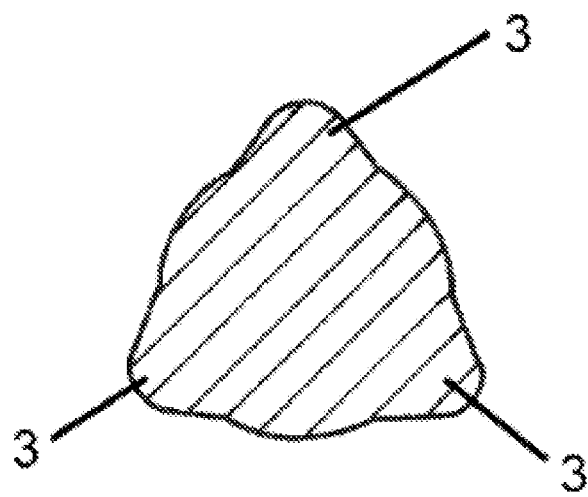
FIG. 2 shows the first embodiment of the invention in a cross-sectional view.

FIG. 2 shows the proximal shaft (1) of the first embodiment in a cross-sectional view. In this case, the three fixing aids (3) are also shown, which are arranged at equal distances around the proximal shaft (1).

Figure 3:
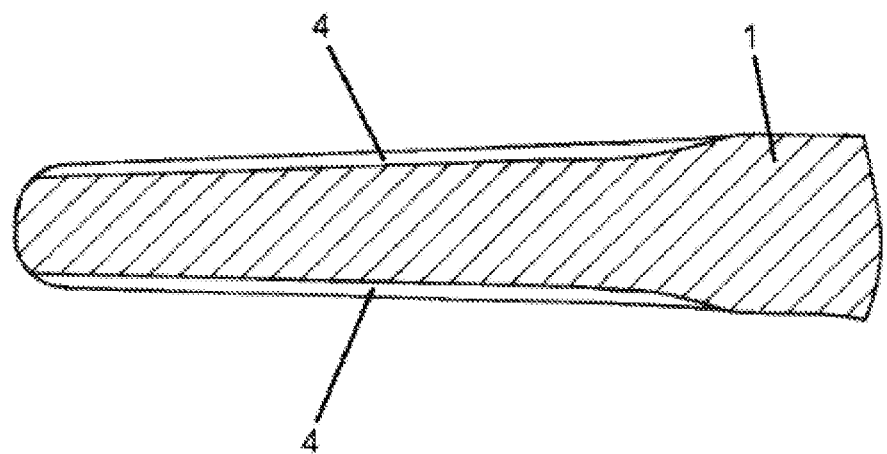
FIG. 3 shows the proximal shaft (1) of the first embodiment in a longitudinal sectional view.

FIG. 3 shows the proximal shaft (1) in a cross-sectional view. The profile of the longitudinal groove (4) can be produced using a radius milling cutter.

Figure 4:
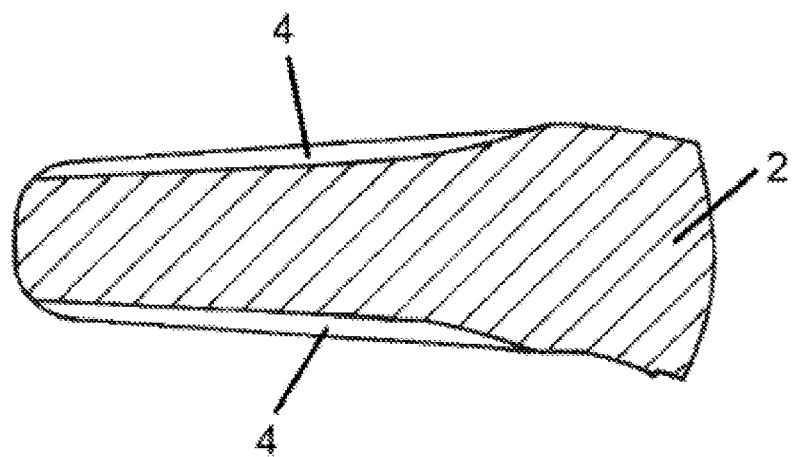
FIG. 4 shows the distal shaft (2) of the first embodiment of the invention in a longitudinal sectional view.

FIG. 4 shows the distal shaft (2) in a cross-sectional view. The distal shaft (2) is also provided with longitudinal grooves (4).

Figure 5:
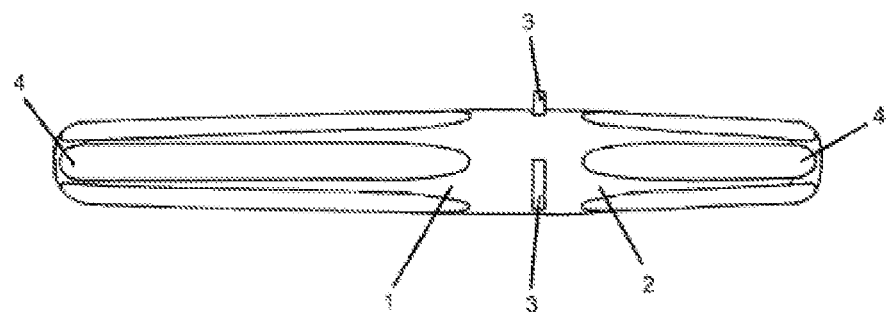
FIG. 5 shows a second embodiment of the invention in a side view.

FIG. 5 shows a second embodiment of the invention. The magnesium alloy used for production contains 0.10 to 2.50 wt. % zirconium, 0.01 to 0.80 wt. % zinc, 1.50 to 5.00 wt. % yttrium and 2.50 to 5.00 wt. % further rare earth metals. There is an angle of 180 degrees between the proximal shaft (1) and the distal shaft (2). Otherwise, this embodiment corresponds to the first embodiment with respect to its dimensions.

Figure 6:
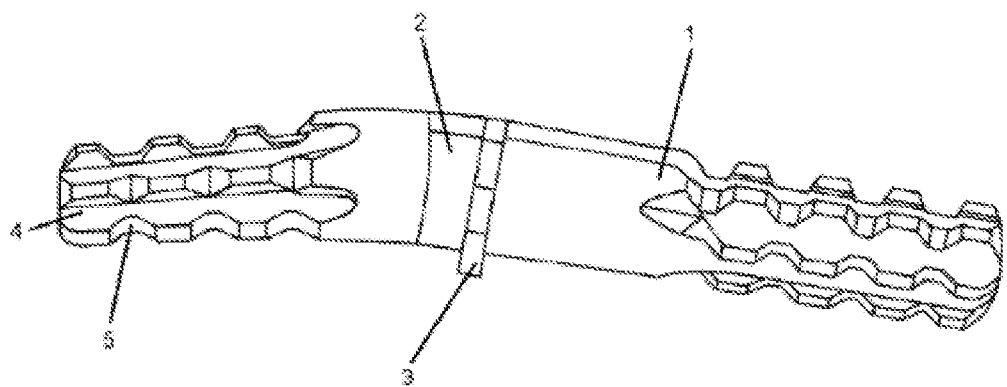
FIG. 6 shows a third embodiment of the invention in a side view.

FIG. 6 shows a third embodiment of the invention. The magnesium alloy used for production contains 0.10 to 2.50 wt. % zirconium, 0.01 to 0.80 wt. % zinc, 1.50 to 5.00 wt. % yttrium and 2.50 to 5.00 wt. % further rare earth metals. The proximal shaft (1) and distal shaft (2) have both longitudinal grooves (4) and transverse grooves (5). The transverse grooves (5) lend the implant an improved hold in the bone.

REFERENCE LIST

1. Proximal shaft
2. Distal shaft
3. Fixing aid
4. Longitudinal groove
5. Transverse groove

The invention claimed is:
1. A proximal interphalangeal (PIP) implant or a distal interphalangeal (DIP) implant for osteosynthesis during arthrodesis of a joint and for the osteosynthesis and stabilization of fractures of bones of the human skeleton, the PIP implant or the DIP implant comprising:
   a conical shaft comprising a conical proximal shaft (1) and a conical distal shaft (2), which are connected together at an angle of 155 degrees to 175 degrees, wherein each of the proximal shaft and the distal shaft (1, 2) has at least one longitudinal groove (4), and
   at least two fixing aids (3) between the shafts (1, 2), the at least two fixing aids protruding beyond a diameter of the shafts (1, 2),
   wherein the at least two fixing aids (3) are arranged at equal distances around the shafts, each of the at least two fixing aids (3) including one or more of the following: a wing extension, a lug, a rail, a score or a fixation point,
   wherein a length of the proximal shaft (1) is 10.00 millimeters (mm) to 15.00 mm, a length of the distal shaft (2) is 5.00 mm to 11.00 mm, a diameter of each of the proximal shaft and the distal shaft (1, 2) is 2.40 mm to 3.60 mm, a thickness of the at least two fixing aids (3) is 0.10 mm to 2.00 mm, and an overhang of the at least two fixing aids (3) over the diameter of each of the proximal shaft and the distal shaft (1, 2) is 0.25 mm to 4.00 mm,
   wherein the length of the distal shaft is shorter than the length of the proximal shaft, and
   the implant comprises a magnesium-based alloy which is resorbable by a human body and comprises 0.10 wt. % to 2.50 wt. % zirconium, 0.01 wt. % to 0.80 wt. % zinc, 1.50 wt. % to 5.00 wt. % yttrium and 2.50 wt. % to 5.00 wt. % other rare earth metals, and a copper and aluminum content less than 0.20 wt. %.

2. The PIP implant or the DIP implant according to claim 1, wherein each of the proximal shaft and the distal shaft (1, 2) has two to eight longitudinal grooves.

3. The PIP implant or the DIP implant according to claim 1, wherein the at least two fixing aids (3) are symmetrically arranged around the proximal shaft and the distal shaft (1, 2).

4. The PIP implant or the DIP implant according to claim 3, wherein a thickness in the cross-section of each of the fixing aids (3) is between 0.20 mm and 2.00 mm, and each fixing aid (3) protrudes radially beyond the proximal shaft and the distal shaft (1, 2) by 0.50 mm to 4.00 mm.

5. The PIP implant or the DIP implant according to claim 4, wherein the thickness in the cross-section of each fixing aid (3) is between 0.20 mm and 1.00 mm, and each fixing aid (3) protrudes radially beyond the proximal shaft and the distal shaft (1, 2) by 0.50 mm to 2.00 mm.

6. The PIP implant or the DIP implant according to claim 5, wherein the thickness in the cross-section of each fixing aid (3) is between 0.20 mm and 0.80 mm, and each fixing aid (3) protrudes radially beyond the proximal shaft and the distal shaft (1, 2) by 0.50 mm to 1.00 mm.

7. The PIP implant or the DIP implant according to claim 1, wherein the thickness of the at least two fixing aids (3) is 0.20 mm to 1.00 mm and the overhang of the at least two fixing aids (3) over the diameter of each of the proximal shaft and the distal shaft (1, 2) is 0.50 mm to 2.00 mm.

8. The PIP implant or the DIP implant according to claim 1, wherein the angle between the proximal shaft and the distal shaft (1, 2) is between 155 degrees to 160 degrees.

9. The PIP implant or the DIP implant according to claim 1, wherein the angle between the proximal shaft and the distal shaft (1, 2) is 160 degrees.

10. The PIP implant or the DIP implant according to claim 1, wherein at least one of the proximal shaft and the distal shaft (1, 2) has a plurality of transverse grooves (5).

11. The PIP implant or the DIP implant according to claim 1, wherein the magnesium-based alloy comprises 0.10 wt. % to 1.00 wt. % zirconium, 4.75 wt. % to 5.00 wt. % yttrium, and 2.00 wt. % to 4.00 wt. % other rare earth metals.

12. The PIP implant or the DIP implant according to claim 1, wherein the magnesium-based alloy comprises 0.10 wt. % to 1.00 wt. % zirconium, 3.70 wt. % to 4.30 wt. % yttrium, and 2.50 wt. % to 4.40 wt. % other rare earth metals.

13. The PIP implant or the DIP implant according to claim 1, wherein the magnesium-based alloy comprises less than 0.10 wt. % copper, iron, nickel and aluminum.

14. The PIP implant or the DIP implant according to claim 13, wherein the magnesium-based alloy comprises less than 0.01 wt. % aluminum, less than 0.20 wt. % zinc, less than 0.15 wt. % manganese, less than 0.20 wt. % lithium, less than 0.01 wt. % silicon, less than 0.01 wt. % iron, less than 0.03 wt. % copper, and less than 0.005 wt. % nickel.

15. The PIP implant or the DIP implant according to claim 1, wherein each of the proximal shaft and the distal shaft (1, 2) has six longitudinal grooves.

16. The PIP implant or the DIP implant according to claim 1, wherein three fixing aids (3) are symmetrically arranged around the proximal shaft and the distal shaft (1, 2).

* * * * *